United States Patent
Dalvit et al.

(10) Patent No.: US 7,255,985 B2
(45) Date of Patent: Aug. 14, 2007

(54) FLUORINE NMR SPECTROSCOPY FOR BIOCHEMICAL SCREENING

(75) Inventors: Claudio Dalvit, Milan (IT); Elena Ardini, Milan (IT); Maria Magdalena Flocco, Milan (IT); Gianpaolo Fogliatto, Varese (IT); Nicola Mongelli, Milan (IT); Marina Veronesi, Milan (IT)

(73) Assignee: Pfizer Italia S.r.l., Rome (IT)

( * ) Notice: Subject to any disclaimer, the term of this patent is extended or adjusted under 35 U.S.C. 154(b) by 84 days.

(21) Appl. No.: 10/888,378

(22) Filed: Jul. 9, 2004

(65) Prior Publication Data

US 2005/0048594 A1 Mar. 3, 2005

Related U.S. Application Data

(60) Provisional application No. 60/486,099, filed on Jul. 10, 2003.

(51) Int. Cl.
*C12Q 1/00* (2006.01)
*C12Q 1/48* (2006.01)

(52) U.S. Cl. .................................. 435/4; 435/15
(58) Field of Classification Search ............... None
See application file for complete search history.

(56) References Cited

OTHER PUBLICATIONS

On-Line Medical Dictionary definition for "deconvolution".*
Reuveni et al., "Toward a PKB Inhibitor: Modification of a Selective PKA Inhibitor by Rational Design", Biochemistry 41: 10304-10314 (2002).*
Percival et al., "19F NMR Investigations of the Catalytic Mechanism of Phosphoglucomutase Using Fluorinated Substrates and Inhibitors", Biochemisty 31: 505-512 (1992).*

* cited by examiner

*Primary Examiner*—Sandra E. Saucier
(74) *Attorney, Agent, or Firm*—Scully, Scott, Murphy & Presser, P.C.

(57) ABSTRACT

High-Throughput Screening (HTS) of large compound libraries is the method of drug-lead discovery. It is now well accepted that for a functional assay, quality is more important than quantity. A biochemical NMR method originally proposed by Percival and Withers (Biochemistry, 1992, 31, 498–505) is extended to the screening of Ser/Thr kinases. The method requires the presence of a $CF_3$ (or CF) moiety on the substrate and utilizes $^{19}F$ NMR spectroscopy for the detection of the starting and enzymatically modified substrates. Experiments can be performed in real time or in an endpoint assay format using protein and substrate concentrations comparable to the ones used by other HTS techniques. Application of this technique to the phosphorylation of a substrate by the protein Ser/Thr kinase AKT1 is presented.

6 Claims, 5 Drawing Sheets

SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: CF3-labeled substrate

<400> SEQUENCE: 1

Ala Arg Lys Arg Glu Arg Ala Tyr Ser Phe Gly His His Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: CF3-labeled substrate

<400> SEQUENCE: 2

Ala Arg Lys Arg Glu Arg Ala Phe Ser Phe Gly His His Ala
1               5                   10

FLUORINE NMR SPECTROSCOPY FOR BIOCHEMICAL SCREENING

CROSS REFERENCE TO RELATED APPLICATIONS

The present application claims benefit of U.S. Provisional Application No. 60/486,099 filed Jul. 10, 2003.

BACKGROUND OF THE INVENTION

The testing of a large number of molecules in an appropriate biochemical or cellular assay is usually one of the first steps in a drug discovery project [Smith A. Nature 418, 453–459 (2002)]. Screening based on Fluorescence Polarization (FP) [Checovich, W. J. et al. Nature 375, 254–256. (1995); Pope, A. J. et al. Drug Discov. Today 4, 350–362 (1999)], Fluorescence Resonance Energy Transfer (FRET), Homogeneous Time-Resolved Fluorescence (HTRF) and the traditional Scintillation Proximity Assay (SPA) are nowadays the technologies of choice for a biochemical assay [Parker, G. J. et al. J. Biomol. Screening 5, 77–88 (2000)]. The sensitivity and miniaturized format of these methodologies allow for the high throughput screening (HTS) of large proprietary compound collections. However, the complexity of the assays utilized in HTS often results in a large number of hits that are then not confirmed in a subsequent secondary assay. It is now well accepted that for screening, quality is more important than quantity [Smith A. Nature 418, 453–459 (2002)]. Therefore, ways of making the biochemical assays for identification of new lead molecules more reliable are in continual development.

Over the last few years Nuclear Magnetic Resonance (NMR)-based screening has emerged as a powerful tool for lead molecule identification [Hajduk, P. J. et al. Quarterly Reviews of Biophysics 32, 211–240 (1999); Stockman, B. J. et al. Prog. NMR Spectr. 41, 187–231 (2002); Meyer, B. et al. Chem. Int. Ed. 42, 864 (2003)]. Although NMR has been applied extensively for characterizing the products of an enzymatic reaction or to gain insight into the kinetics of the reactions [Percival, M. D. & Withers, S. G. Biochemistry 31, 505–512 (1992)], NMR-based biochemical screening that measures the inhibition or the activation of an enzyme for the identification of new lead molecules has found limited applications [Chiyoda T. et al. Chem. Pharm. Bull. 46, 718–720 (1998)]. The low sensitivity limits NMR to enzymatic reactions with very high substrate concentration. Nonetheless, when NMR is compared to the other techniques utilized in HTS, it provides a more reliable array of data. NMR techniques monitor ligand binding to the receptor via the small molecule signals or the protein signals.

Recent developments using $^1$H and in particular $^{19}$F NMR competition binding experiments have allowed for a reduction of substrate and protein consumption for the screening. In addition, these experiments provide with a single point measurement the value of the binding constant of the identified ligand. Percival and Withers used a NMR method to study binding of an enzyme to its fluorinated substrate analogues [Percival, M. D. & Withers, S. G. Biochemistry 31, 505–512 (1992)]. Such method utilizes $^{19}$F NMR detection and requires the presence of a fluorine atom on non-peptide substrates. The $^{19}$F signals of the starting and enzymatically transformed substrates are then monitored. Experiments can be performed in real time allowing the observed enzymatic activity to be monitored kinetically or in an endpoint assay format.

SUMMARY OF THE INVENTION

In one aspect the present invention provides a method for identifying kinase inhibitors using NMR technology. In another aspect, the present invention provides kinase inhibitors identified by NMR technology.

The present invention also provides a NMR method to characterize the unknown function of a protein by its interaction with $CF_3$-labeled substrates of other known-function proteins.

BRIEF DESCRIPTION OF THE DRAWINGS

(FIG. 2B bottom) Integral of the phosphorylated peptide as a function of the ATP concentration and the best fit of the experimental data with the derived $K_M$ for ATP of 89+/−17 μM.

(FIG. 3B bottom) Integral of the phosphorylated peptide as a function of the inhibitor concentration and the best fit of the experimental data with the derived $IC_{50}$ for H89 of 0.72+/−0.05 μM.

DETAILED DESCRIPTION OF THE INVENTION

Figure 1:
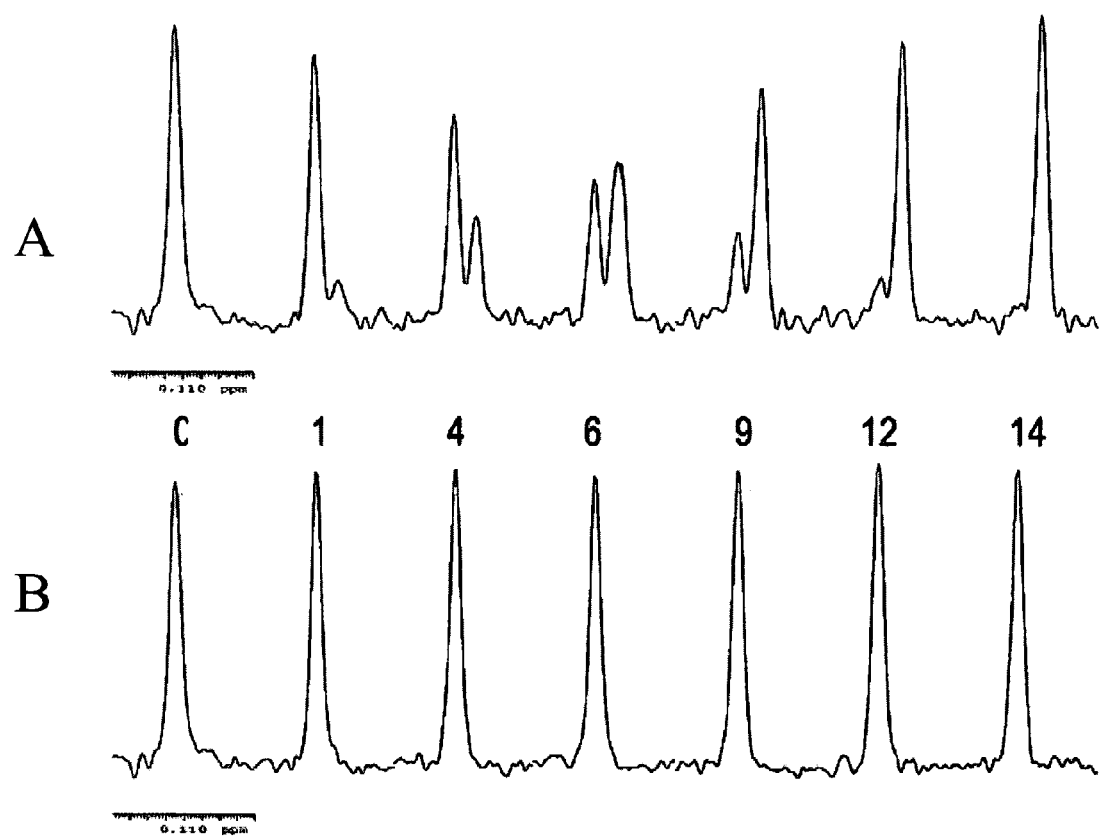
FIG. 1 provides $^{19}$F 564 MHz NMR spectra for the $CF_3$—CO N-capped-AKTide as a function of time (indicated in minutes) after the beginning of the enzymatic reaction. The activated protein, the peptide and ATP concentration were 50 nM, 30 μM and 131 μM, respectively. WtAKT1 recombinant protein was produced by infection of Sf21 insect cells with baculovirus coding for the full length protein fused to the GST moiety at the N-terminus and then purified to homogeneity after removal of the GST tag. The samples were in 50 mM Tris pH 7.5, with 1 mM DTT and 5 mM $MgCl_2$. Spectra were recorded at 20° C. in the absence (FIG. 1A top) and in the presence (FIG. 1B bottom) of 10 μM Staurosporine. A total of 256 scans with 2.8 s repetition time were recorded for each spectrum (12 minutes measuring time). Chemical shifts are referenced to trifluoroacetic acid.

The present invention overcomes the limitations of NMR biochemical screening with respect to protein and substrate concentrations when compared to prior art HTS techniques. The present invention provides a novel and sensitive NMR method in which a moiety with three fluorine atoms ($CF_3$) is used to label a substrate. The use of a $CF_3$-labeled substrate, e.g., a $CF_3$-labeled peptide, allows for rapid and reliable biochemical screening at protein and substrate concentrations comparable to the concentrations utilized by standard HTS techniques. The NMR method of the present invention has unique advantages. i) Fluorine NMR spectroscopy is very sensitive, 0.83 times that of the proton. ii) Fluorine signals appear as sharp singlet resonances (the experiments do not require proton decoupling if the $CF_3$ is not scalar coupled to protons) originating from three fluorine atoms, and therefore, the signal is very intense. This property is crucial for the screening because it permits the use of substrate concentrations that are in the range of its $K_m$ thus allowing detection of medium and weak inhibitors iii) There are no spectral interferences from protonated solvents, buffers, or detergents typically used in enzymatic reactions. Overlap with the signals of the substrate in the presence of the $CF_3$-containing molecules represents an extremely rare event due to the limited number of sharp singlet $^{19}F$ signals (molecules will typically have one $CF_3$ group) and the large dispersion of the $^{19}F$ chemical shift. iv) The $^{19}F$ isotropic chemical shift is very sensitive to the chemical environment [Gerig, J. T. Prog. NMR Spectrosc. 26, 293–370 (1994)] resulting in differential chemical shifts for the starting and enzymatically transformed substrate resonances thus allowing a direct comparison of their intensities.

In one embodiment of the present invention, NMR has been utilized to measure the phosphorylation of a $CF_3$-labeled substrate by the protein Ser/Thr kinase AKT1. Protein kinase AKT1 is an anti-apoptotic protein kinase that has an elevated activity in a number of human malignancies [Staal, S. P. et al. J. Exp. Med. 167, 1259–1264 (1988); Bellacosa, A. Et al. Science 254, 274–277 (1991)]. The substrate AKTide is a peptide of 14 aminoacids [Obata, T. et al. J. Biol. Chem. 46, 36108–36115 (2000)] that was labeled with a $CF_3$ moiety by N-terminal capping with trifluoroacetic anhydride resulting in the peptide ($CF_3$—CO—ARKRERAYSFGHHA) (Seq ID NO:1). Alternatives can include the introduction of the $CF_3$ group at the C-terminal via amide formation with a trifluoromethylamine or the substitution of one amino acid during the peptide synthesis with a fluorinated ($CF_3$) amino acid (e.g. Tyr with para-$CF_3$ Phe). The $CF_3$ at the N terminal, the C terminal or the substituted amino acid (the para-$CF_3$ Phe points toward the solvent, while the Ser to be phosphorylated points toward the enzyme), is located away from the serine phosphorylation site and therefore does not interfere with the binding. In the case of non-peptidic substrates, chemical synthesis is required for the introduction of the $CF_3$ moiety in the appropriate position in the substrate.

An enzymatic reaction was performed by incubating the unphosphorylated $CF_3$-labeled peptide of Seq ID NO:1 in the presence of ATP and activated protein kinase AKT1. The conversion of unphosphorylated peptide to phosphorylated peptide generated a shift of the 19F signal as indicated in FIG. 1 (top), which shows the $^{19}F$ spectrum containing the signal of the $CF_3$ moiety of the substrate as a function of time after the start of the enzymatic reaction. At time 0 only one signal is observed corresponding to the unphosphorylated species of the peptide. With time the signal of the unphosphorylated peptide decreases and a new signal appears in the spectrum corresponding to the phosphorylated peptide. The sum of the two integral signals at any time after the start of the reaction corresponds to the signal integral of the unphosphorylated peptide at time 0. The enzymatic reaction is complete after 149 minutes and only the signal of the phosphorylated peptide is visible in the spectrum.

The same reaction performed in the presence of the strong inhibitor staurosporine did not result in any formation of phosphorylated peptide as is evident in FIG. 1 (bottom). Despite the large distance of the $CF_3$ group from the phosphorylation site, the chemical shifts of this moiety in the phosphorylated and unphosporylated peptides are different.

As a screening method, the reaction can also be carried out in the presence of a mixture of compounds containing an inhibitor. Then, deconvolution of the active mixture is performed to identify which of the compounds in the mixture is the inhibitor. In accordance with the present invention, deconvolution means that the reaction is performed repeatedly in the presence of the mixture and in the absence of each one of the compounds. That is, there is no inhibition when the reaction in is carried out in the presence of the mixture minus the inhibitory compound. To confirm the inhibitory effect of one of the compounds, inhibition can be observed when the reaction is also performed in the presence of the single inhibitory compound that was identified from the mixture. As an example, the reaction of unphosphorylated CF3-labeled peptide of Seq ID NO:1, ATP, and activated protein kinase AKT1 was also performed in the presence of a five molecule mixture containing the compound H89 [Reuveni, H. et al. Biochemistry 41, 10304–10314 (2002)], an AKT1 inhibitor. The result was inhibition of peptide phosphorylation. There was no inhibition of peptide phosphorylation when this reaction was carried out in the presence of the mixture in the absence of H89. The inhibitory effect over peptide phosphorylation of H89 was confirmed when the reaction was performed in the presence of only H89.

For screening purposes and $IC_{50}$ measurements the reaction is typically stopped after an established delay that will depend on the enzyme and ATP concentrations and $K_{cat}$. The reaction can be quenched either by adding a concentrated solution of EDTA or by denaturating the protein. In accordance with the present invention, however, a more economical method is employed to quench reaction, namely the addition of about 5 to about 10 μM of the strong inhibitor staurosporine ($IC_{50}$ in the low nM range). Even after several hours from the addition of staurosporine no changes of the $^{19}F$ spectrum were observed. After the quench, the signal intensity ratio of the two $^{19}F$ signals is monitored. In the absence of an inhibitor the signal intensity ratio $I_{(p)}/I_{(unP)}$ corresponds to 0% inhibition whereas when the ratio is 0 it corresponds to 100% inhibition. This method is valid only if the peptide concentration is always the same otherwise the signal integral of the phosphorylated peptide should be monitored.

Figure 2:
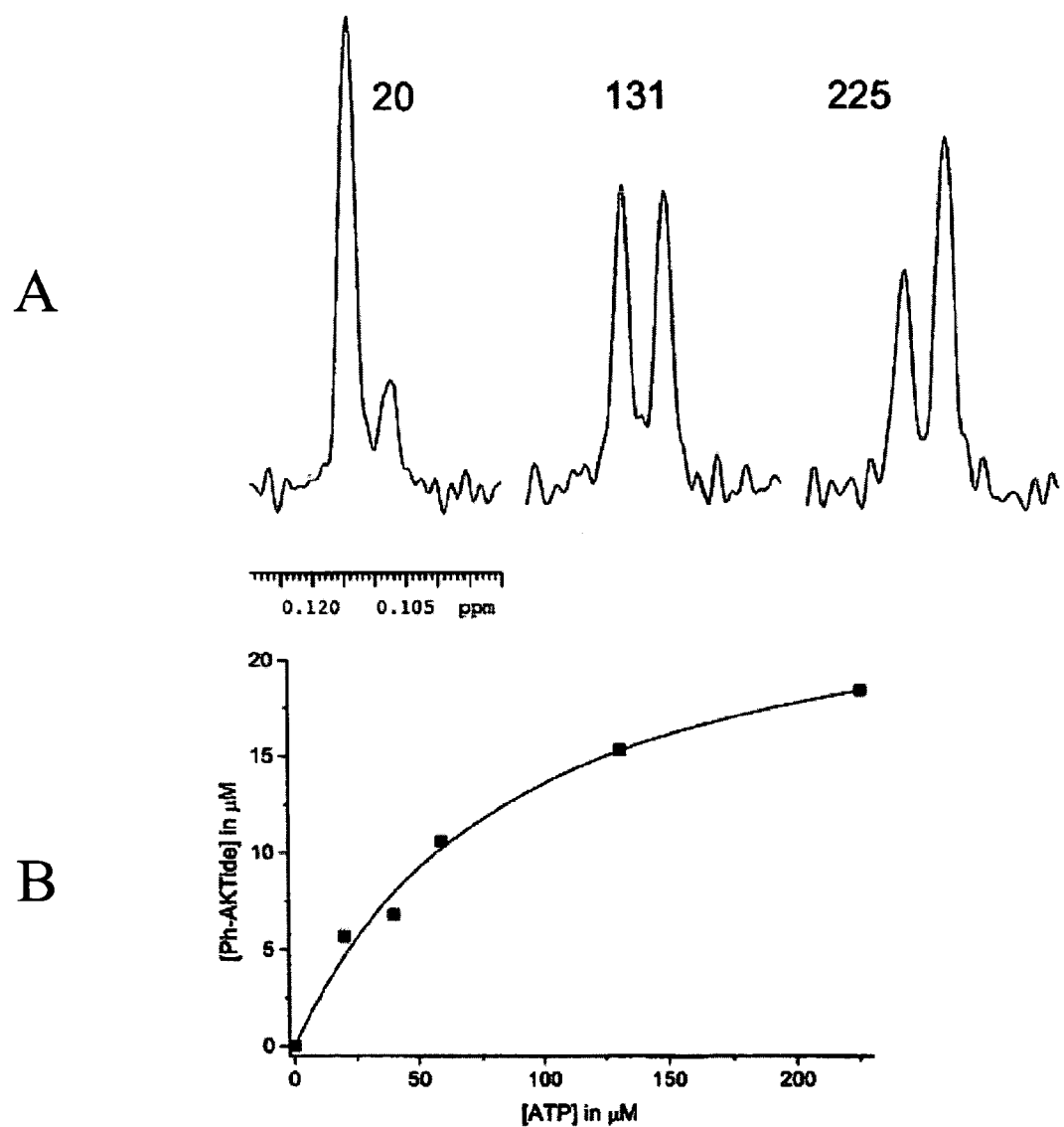
FIG. 2 provides (FIG. 2A top) $^{19}$F 564 MHz NMR spectra for the $CF_3$—CO N-capped-AKTide recorded with three different concentrations (indicated in μM) for ATP. The activated protein and the peptide concentrations were 40 nM and 30 μM, respectively. The samples were in 50 mM Tris pH 7.5, with 1 mM DTT and 5 mM $MgCl_2$. The reaction was run at 22° C. and quenched after 60 minutes with the addition of 10 μM staurosporine.

The dissociation binding constant of ATP must be calculated first in order to optimize the ATP concentration used for the screening experiments and for deriving the binding constant of the hits from their $IC_{50}$. For this purpose reactions at different ATP concentrations are recorded [Fersht, A. Enzyme Structure and Mechanism, W. H. Freeman and Company, New York 1985]. The signal intensity of the phosphorylated peptide as a function of the ATP concentration is shown in FIG. 2. Fitting of the experimental data results in a binding constant for ATP (in the presence of 30 µM substrate) of 89+/−17 µM.

Figure 3:
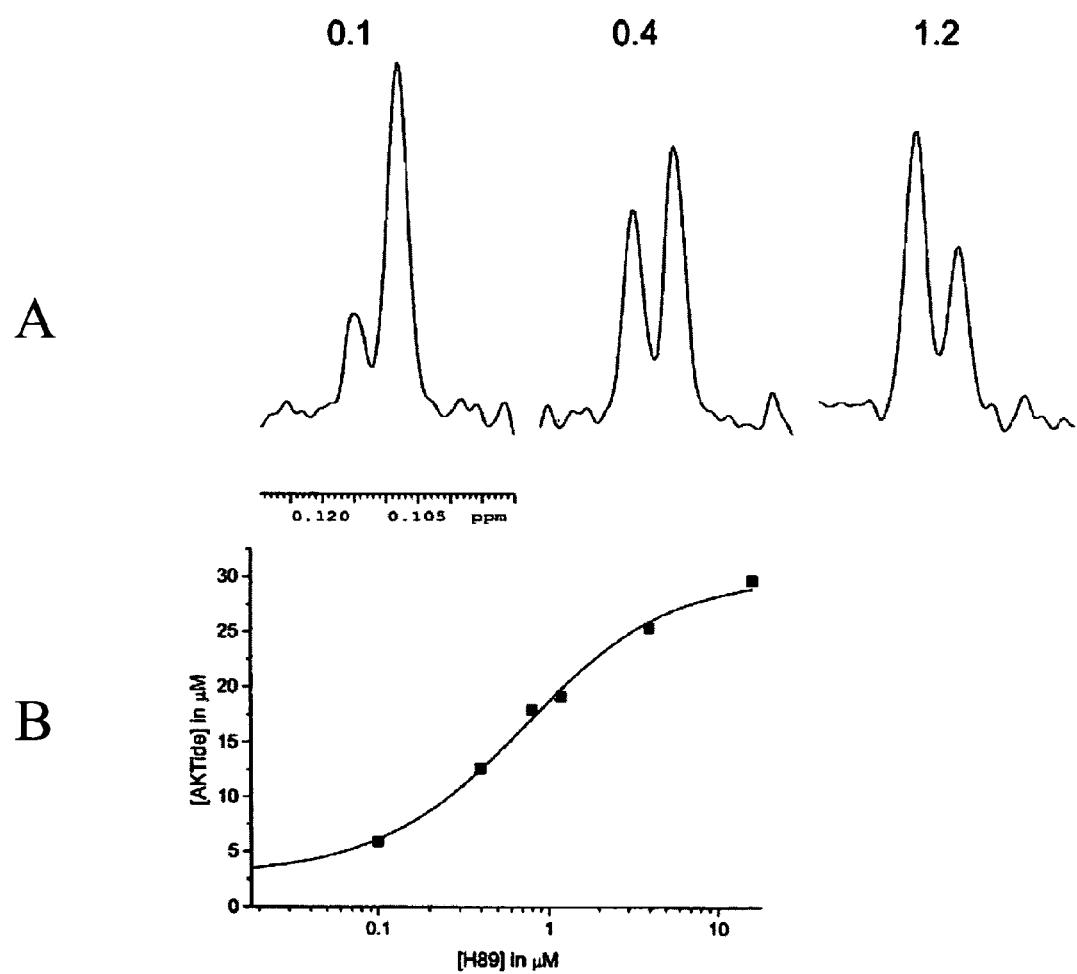
FIG. 3 provides (FIG. 3A top) $^{19}$F 564 MHz NMR spectra for the $CF_3$—CO N-capped-AKTide recorded with three different concentrations (indicated in μM) for the inhibitor H89. The activated protein, the peptide and ATP concentration were 40 nM, 30 μM and 131 μM, respectively. The samples were in 50 mM Tris pH 7.5, with 1 mM DTT and 5 mM $MgCl_2$. The reaction was run at 22° C. and quenched after 120 minutes with the addition of 10 μM staurosporine.
Figure 5:
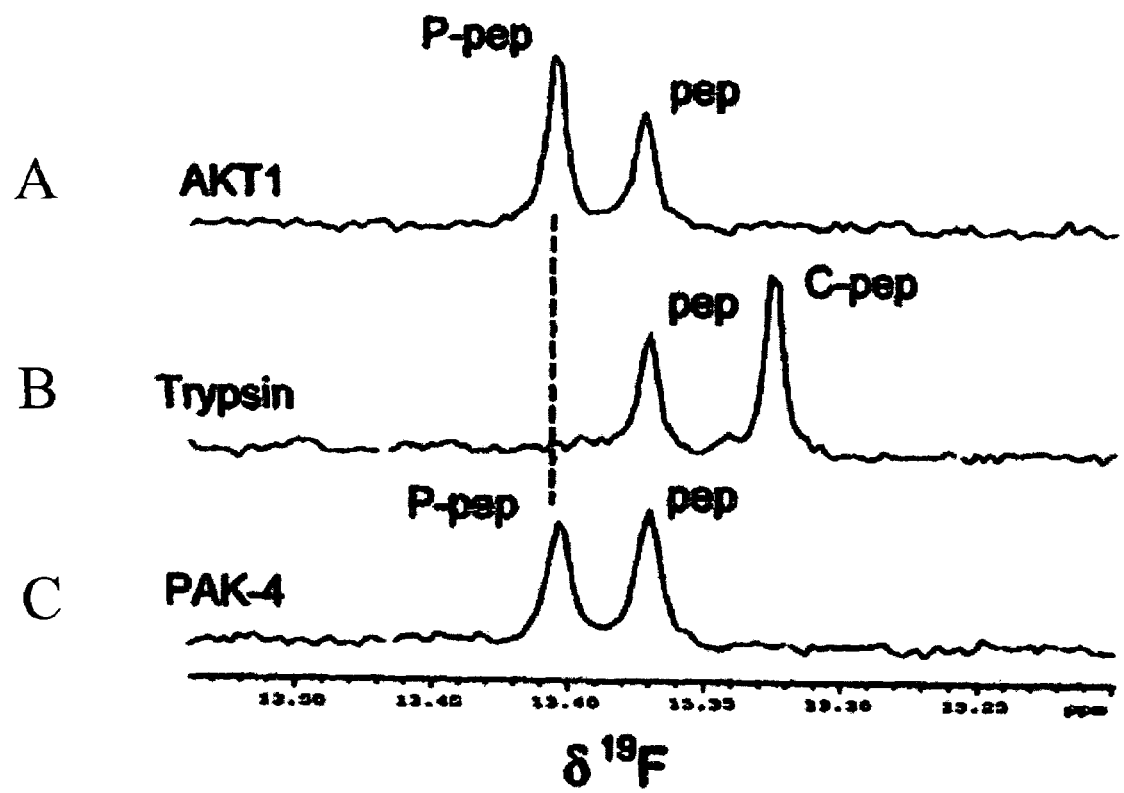
FIG. 5 provides the 19F spectra of the peptide of Seq ID NO:2 in the presence of three different proteins, 25 nM AKT1 (FIG. 5A top), 15 nM trypsin (FIG. 5B middle) and 150 nM PAK4 (FIG. 5C bottom). The peptide is a good substrate for AKT1 and trypsin. The chemical shift of the cleaved peptide is quite different when compared to the chemical shift of the phosphorylated peptide. The reaction performed in the presence of p-21 activated protein PAK4 results in the appearance of a signal at the chemical shift of the phosphorylated peptide.

In accordance with the present invention, screening is first performed at a single concentration for the compounds in the library. Compounds can be screened in small or large mixtures. For example, if only strong inhibitors with $IC_{50}$ <5 µM will be considered, then it will be sufficient to use molecules at about a 5 µM concentration. In practice, the reliability of the method of the present invention allows the identification of a weaker inhibitor with, e.g., an $IC_{50}$ in the range of 10–20 µM even when the concentration of the screened molecules is only about 5 µM. As FIG. 5 shows, substrate concentrations can be as low as about 10–20 nM. This low concentration allows the preparation of mixtures with a large number of components without severe problems of aggregation or solubility. Deconvolution of the active mixture is then carried out for the identification of the inhibitor. For the characterization of the $IC_{50}$ of the hits, experiments at different inhibitor concentrations are then performed as shown in FIG. 3 for the compound H89 [Reuveni, H. et al. Biochemistry 41, 10304–10314 (2002)]. In the absence of allosteric effects a meaningful $IC_{50}$ value is derived with a single point measurement. A $CF_3$-labeled ATP analogue can also be used with the method of the present invention. In this case, the $^{19}F$ signals of ATP and ADP are monitored. Inhibitors that bind in the ATP binding pocket or inhibitors that compete with the peptide for the substrate binding site can be identified.

The method of the present invention therefore represents a simple and reliable assay because it is homogeneous and directly detects both the phosphorylated and unphosphorylated substrate. The $^{19}F$ NMR assay does not require i) the presence of secondary reactions performed with enzymes or specific antibodies or ii) separation and/or washing steps necessary for the readout with other methods. The method's simplicity results in reliable lead molecule identification and quantification of the molecules' inhibitory activity. Compounds displaying only a weak inhibitory activity can also be safely selected. Small chemical changes of the weak inhibitors or the selection of similar molecules bearing the same scaffold might result in the identification of potent inhibitors.

In other art recognized HTS techniques, often the real concentration differs from the nominal concentration. A large difference in compound concentration results in a significant error of the derived $IC_{50}$. The causes for concentration differences in other prior art HTS techniques can be ascribed to weighing errors, sample impurity, poor solubility of the compound, and chemical instability in an aqueous environment. In contrast, with the NMR method of the present invention these chemical properties can be easily measured by acquiring, in addition to the fluorine spectrum, also a proton spectrum. Therefore, the real concentration of the inhibitor determined with $^1H$ NMR allows a significantly more accurate measurement of the $IC_{50}$ value.

The method of the present invention is not limited to the identification of inhibitors only, but can also be used for the detection of agonists. In the case of protein kinases the $^{19}F$ signal of the phosphorylated peptide in the presence of an agonist is larger when compared to the same signal of the reference sample (i.e. sample for which the reaction was performed in the absence of compounds to be screened).

The concentration of the protein used with this method can be as low as a few nanomolar, comparing favorably with the concentration used in other HTS techniques. However, the volume necessary for each NMR sample using a 5 mm probe is about 500–550 µL. A 2- to 3-fold volume reduction is achieved in accordance with the present invention with the use of a flow-injection probe or a 3 mm probe. The high sensitivity of the $CF_3$ signal allows for rapid acquisition of the spectra. Further, the same spectra can be recorded even more rapidly with the use of cryogenic technology applied to $^{19}F$ detection. Therefore, under the settings of the current method, the spectra that require an acquisition time of 3 minutes can be recorded in just 12 seconds. Further, the problems of radiation damping encountered in proton-detected experiments recorded with cryoprobes are absent in the fluorine-detected methodology of the present invention because of the low concentration of the $CF_3$-labeled substrate.

Bovine serum albumin (BSA) can be used with the method of the present invention to avoid sticking of the protein to the tube wall [Hlady, V. et al. Curr. Opin. Bioctechnol. 7, 72–77 (1996)]. However, while the enzymatic reaction in the presence of BSA becomes faster due to the fact that all the enzyme is available in solution, the $IC_{50}$ of the compound can become weaker because of the compound sequestering from the solution by BSA. Therefore, the present method performed in the presence or absence of BSA or human serum albumin (HSA), for the compounds in the hit to lead optimization phase, can provide important structural information for designing analogues with retained inhibitory activity to the target enzyme and reduced affinity to albumin.

Figure 4:
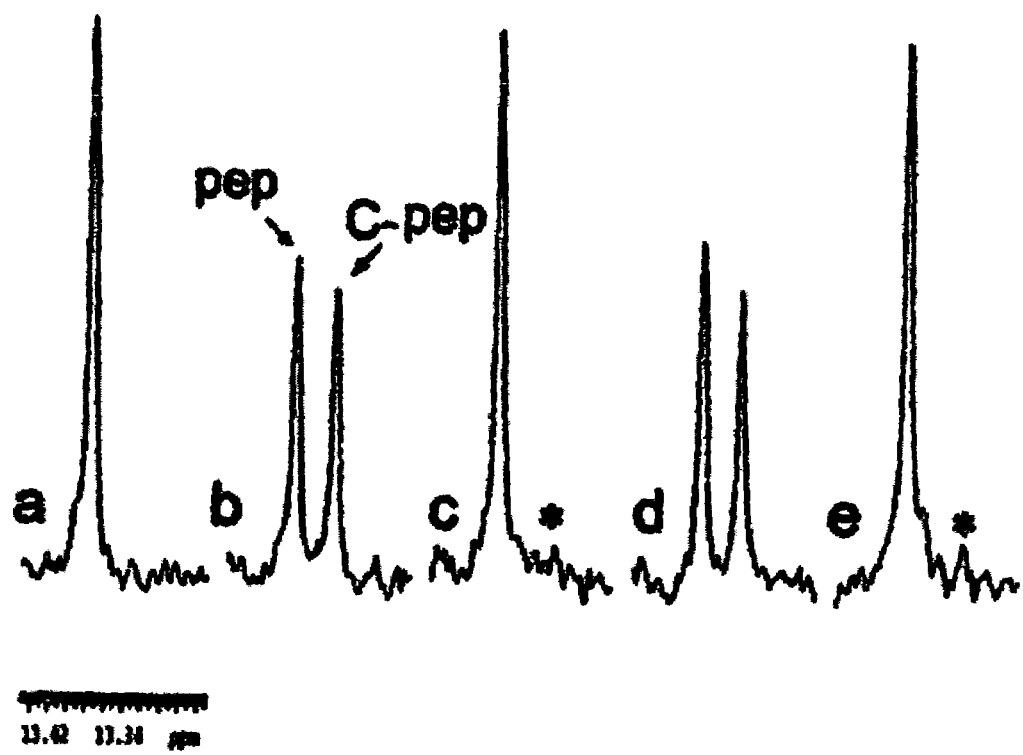
FIG. 4 provides the screening of proteases, where the substrate is the peptide of Seq ID NO:2 and the protein is trypsin from bovine pancreas. $^{19}$F NMR spectra for the peptide in the absence (a) and in the presence (b–e) of trypsin. The reaction was run at 22° C. and quenched after 30 minutes with the addition of 0.5 mM phenylmethylsulfonyl fluoride (PMSF). The reaction was performed in the absence of compound (b), in the presence of a five compound mixture (2-amino-6 methylquinazolin-4 ol, ethyl 2-quinoxalinecarboxylate, 5-methyl-benzimidazole, methyl isoquinoline-3-carboxylate, and leupeptin) (c), in the presence of the same mixture without leupeptin (d), and in the presence of only leupeptin (e). The protein, peptide, and compound concentrations were 15 nM, 30 μM, and 20 μM, respectively. A total of 128 scans with 2.8 s repetition time were recorded for each spectrum (6 minute measuring time). Pep and C-pep are the substrate and the product respectively. The asterisks in (c) and (e) indicate the chemical shift of the missing cleaved peptide signal.

The method of the present invention can also be applied to many different types and subtypes of enzymes (e.g. proteases, phosphatases, ligases, etc.). In another embodiment of the present invention, the screening can be performed with trypsin, a protease that cleaves peptide bonds C-terminally of lysine and arginine [Price, N.C. et al. Fundamentals of Enzymology, Oxford University Press, Oxford, U.K. (1999)], and, as a substrate, the peptide (ARKRERAF(3-$CF_3$)SFGHHA) (Seq ID NO:2). As shown in FIG. 4b, in the presence of trypsin two $^{19}F$ signals are visible in the spectrum at 13.38 and 13.33 ppm originating from the starting peptide and the cleaved peptide, respectively. Screening was performed in an end point assay format where the reaction was quenched after a defined delay using a known trypsin inhibitor (FIG. 4c). Deconvolution of the active mixture was then performed for the identification of the inhibitor (FIG. 4d,e). Therefore, natural product extracts can be easily screened with this method. The components of the active extracts will then be separated via high performance liquid chromatography (HPLC) and tested as single compounds with the method of the present invention for the identification of the compound responsible for the inhibitory activity.

Another application of the method of the present invention is the determination of protein function. In view of the ready availability of high-throughput genome sequencing, thousands of proteins have been identified. However, the function of many of these proteins is unknown. The function of the protein can be inferred from the types of substrates that can be modified. For this purpose, a functional genomic library of $CF_3$-labeled substrates of enzymes of known function is generated. These substrates are first tested on their known respective enzymes to determine the $^{19}$F chemical shifts of the starting and modified substrate. Some substrates can act as substrates for different classes of enzymes. This library of substrates is then screened as single compounds or in small mixtures against the protein with unknown function. The reduction in signal intensity of a $^{19}$F signal and the appearance of a new resonance at a defined chemical shift allows the recognition of the protein function.

In another embodiment of the present invention, three different proteins, AKT1, Trypsin, and p-21 activated protein (PAK4) were incubated with the $CF_3$-labeled peptide of Seq ID NO:2. As shown in FIG. 5, the reaction in the presence of PAK4 results in the appearance of a $^{19}$F signal with a chemical shift similar to the shift of a phosphorylated peptide as with the $^{19}$F signal of the reaction in the presence of AKT1. This result allowed for the classification of PAK4 to the kinase family. A higher concentration of the protein with unknown function and a longer incubation period may be required because the substrate may not be optimal for the protein with unknown function. The speed of the enzymatic reaction of PAK4 is only ½₂ of the speed of AKT1, therefore, the period of time for the reaction in the presence of PAK4 was longer than the period of time for the reaction in the presence of AKT1. The method of the present invention is also applicable to activated enzymes.

The method of the present invention extends the capabilities of NMR to the enzymatic reactions performed by Ser/Thr kinases. The method performs well and provides a reliable array of experimental data.

EXAMPLE 1

Materials and Methods

WtAKT1 recombinant protein were produced by infection of sf21 insect cells with baculovirus coding for the full length protein fused to GST at the N-terminus. The cells were treated with okadaic acid for 4 hours prior to harvesting. This treatment, by inhibiting the cellular phosphatases, increased the total phosphorylation level of the protein leading to the phosphorylation of the two sites critical for AKT activity, threonine 308 in the activation loop and serine 473 in the C terminal hydrophobic motif. Lysis, purification, and removal of the GST tag were performed by following standard procedures. Trypsin, purchased from Roche Molecular Biochemical (Cat. No. 1418025), was dissolved in 1% acetic acid solution at a final stock solution concentration of 8.33 µM.

The serine/threonine p21-activated kinase PAK4 was expressed as a GST fusion protein in *Escherichia coli* and purified to homogeneity after removal of the GST tag.

All the compounds were prepared in DMSO stock solutions (20–40 nM). The peptides of Seq ID NO:1 and Seq ID NO:2 and Leupeptin were prepared in aqueous solutions at a concentration of 10 and 2.1 mM, respectively. The reactions were run in 50 mM Tris pH 7.5 with 1 mM DTT and 5 mM $MgCl_2$ for AKT1 and 50 mM Tris pH 7.5 for trypsin. $D_2O$ was added to the solutions (8% final concentration) for the lock signal. The enzymatic reactions were performed at room temperature in Eppendorf vials and then quenched after a defined delay with the addition of staurosporine for AKT1 and PMSF for trypsin. The solutions were then transferred to 5 mm NMR tubes.

All NMR spectra were recorded at 20° C. with a 600 NMR spectrometer operating at a $^{19}$F Larmor frequency of 564 MHZ. A 5 mm probe tunable to either 19F or $^1$H frequency was used. The instrument was equipped with a sample management system (SMS) autosampler for automatic data collection. The data were acquired without proton decoupling with an acquisition time of 0.8 seconds and a relaxation delay of 2.8 seconds. Chemical shifts are referenced to trifluoroacetic acid.

The invention claimed is:

1. A method for identifying inhibitors of an enzyme comprising:
   a) labeling a substrate of an enzyme with a $CF_3$ moiety;
   b) measuring an intensity of a $^{19}F$ signal for said $CF_3$-labeled substrate in the presence of said enzyme over a period of time whereby said period of time is the time length required for conversion of an unmodified $CF_3$-labeled substrate into a modified $CF_3$-labeled substrate by said enzyme;
   c) measuring an intensity of a $^{19}F$ signal for said $CF_3$-labeled substrate in the presence of said enzyme and an inhibitor of said enzyme over said period of time; and
   d) identifying the inhibitor of said enzyme by comparing the $^{19}F$ signal intensities measured in steps (b) and (c).

2. The method according to claim 1, wherein said enzyme is a kinase.

3. The method of claim 1, wherein in step (c), the inhibitor of said enzyme is contained in a mixture of compounds, and wherein the $^{19}F$ signal intensity for the $CF_3$-labeled substrate is repeatedly measured in the presence of the enzyme and said mixture in the absence of each compound contained by said mixture so as to determine which compound in said mixture is the inhibitor of said enzyme.

4. A method for identifying agonists of an enzyme comprising:
   a) labeling a substrate of an enzyme with a $CF_3$ moiety;
   b) measuring an intensity of a $^{19}F$ signal for said $CF_3$-labeled substrate in the presence of said enzyme over a period of time whereby said period of time is the time length required for conversion of an unmodified $CF_3$-labeled substrate into a modified $CF_3$-labeled substrate by said enzyme;
   c) measuring an intensity of a $^{19}F$ signal for said $CF_3$-labeled substrate in the presence of said enzyme and an agonist of said enzyme over said period of time; and
   d) identifying the agonist of said enzyme by comparing the $^{19}F$ signal intensities measured in steps (b) and (c).

5. The method according to claim 4, wherein said enzyme is a kinase.

6. The method of claim 4, wherein in step (c), the agonist of said enzyme is contained in a mixture of compounds, and wherein the $^{19}F$ signal intensity for the $CF_3$-labeled substrate is repeatedly measured in the presence of the enzyme and said mixture in the absence of each compound contained by said mixture so as to determine which compound in said mixture is the agonist of said enzyme.

* * * * *